(12) United States Patent
Blum

(10) Patent No.: US 8,298,410 B2
(45) Date of Patent: Oct. 30, 2012

(54) FILTER AND STERILIZATION APPARATUS

(76) Inventor: Holger Blum, Teufen (DE)

( * ) Notice: Subject to any disclaimer, the term of this patent is extended or adjusted under 35 U.S.C. 154(b) by 455 days.

(21) Appl. No.: 12/521,159

(22) PCT Filed: Dec. 19, 2007

(86) PCT No.: PCT/EP2007/011204
§ 371 (c)(1),
(2), (4) Date: Jun. 25, 2009

(87) PCT Pub. No.: WO2008/077565

PCT Pub. Date: Jul. 3, 2008

(65) Prior Publication Data

US 2010/0018913 A1    Jan. 28, 2010

(30) Foreign Application Priority Data

Dec. 27, 2006  (DE) .......................... 20 2006 019 492

(51) Int. Cl.
*B01D 21/30* (2006.01)
*B01D 29/00* (2006.01)

(52) U.S. Cl. ........ 210/136; 210/205; 210/206; 210/209; 210/163

(58) Field of Classification Search .................. None
See application file for complete search history.

(56) References Cited

U.S. PATENT DOCUMENTS

| 5,211,847 A | * | 5/1993 | Kanow | ........................... 210/610 |
| 5,217,607 A | * | 6/1993 | Dalton et al. | ................. 210/143 |
| 6,803,587 B2 | * | 10/2004 | Gadgil et al. | ................. 250/434 |
| 2005/0263447 A1 | | 12/2005 | McGrew, Jr. | |

FOREIGN PATENT DOCUMENTS

| DE | 9320594 U1 | 2/1995 |
| DE | 10005079 A1 | 8/2001 |
| DE | 102004051621 A1 | 4/2006 |

OTHER PUBLICATIONS

PCT International Search Report, PCT Application No. PCT/EP07/11204.
PCT Written Opinion of the International Searching Authority, PCT Application No. PCT/EP07/11204.
PCT International Preliminary Report on Patentability, PCT Application No. PCT/EP07/11204.

* cited by examiner

*Primary Examiner* — Vickie Kim
*Assistant Examiner* — Dirk Bass
(74) *Attorney, Agent, or Firm* — Nawrocki, Rooney & Sivertson, P.A.

(57) ABSTRACT

A filter- and sterilizing apparatus comprising a gravity filter device with a liquid supply (L1), a downpipe filter (F) and a clean liquid drainage (L3) as well as a sterilizing device (U) hydraulically connected to the downpipe filter, is characterized in that the sterilizing device connected to the clean liquid circuit (L3) of the downpipe filter (F), is adjustable in height and has the shape of a supply channel to the overflow weir (Y), wherein the liquid level in the supply channel (K) before starting the filtration is approximately adjustable to the same height with the water level in the downpipe filter (F) above the filter medium (M). The sterilizing device (U) is an ultraviolet sluice.

7 Claims, 2 Drawing Sheets

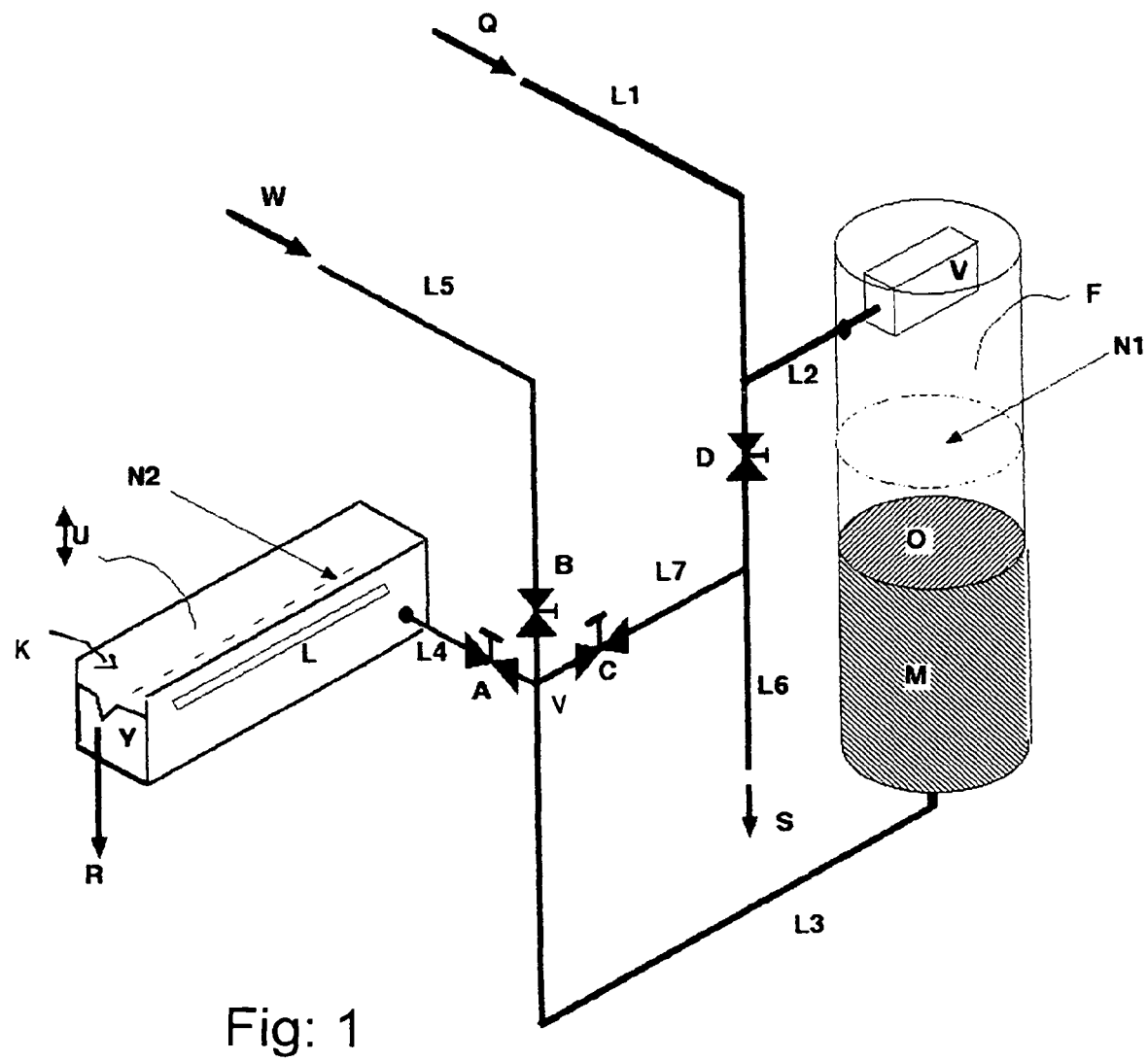
Fig: 1

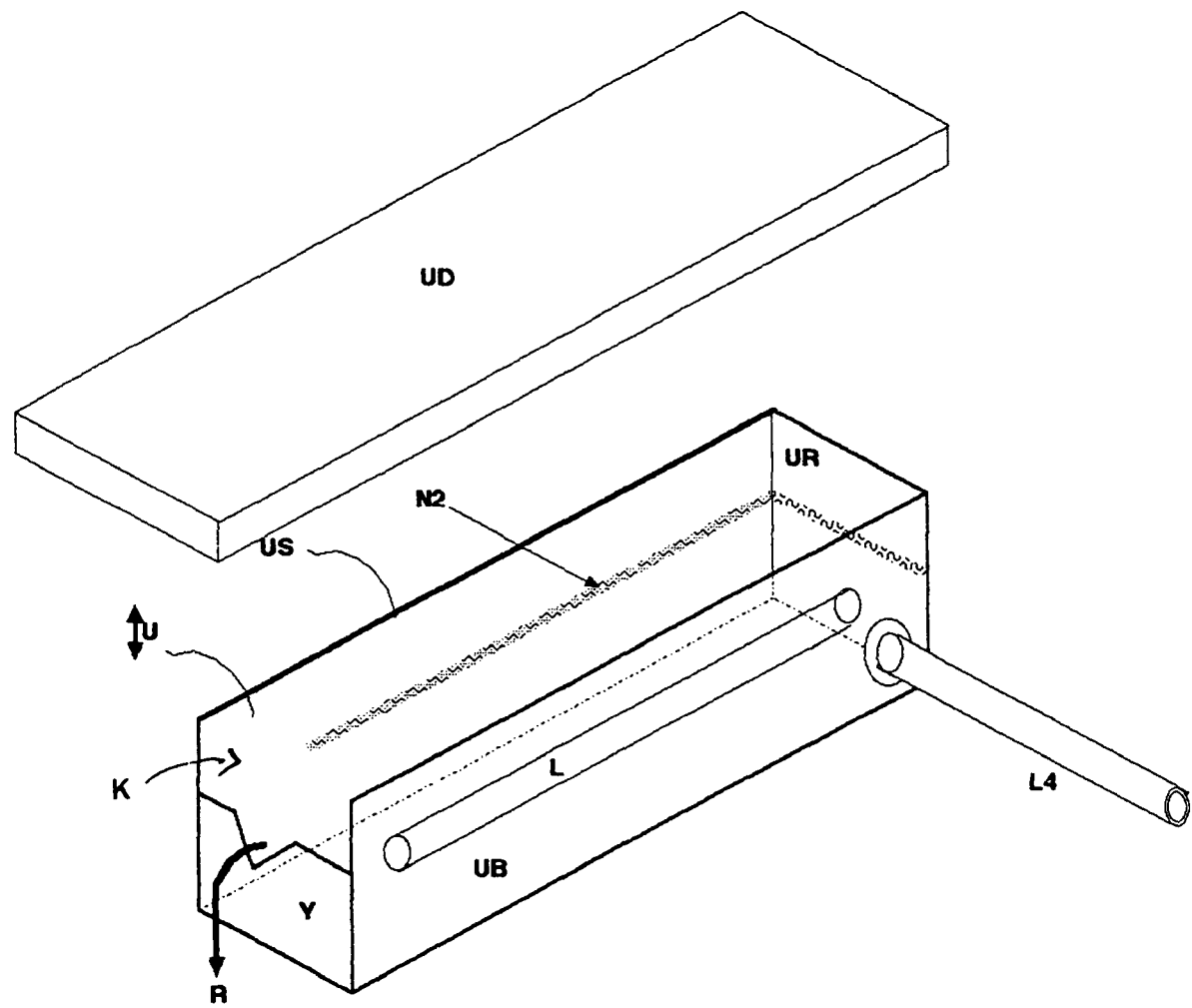
Fig: 2

FILTER AND STERILIZATION APPARATUS

As it is known, a downpipe filter device consists out of three essential components, the filter tank having a drain outlet collector, the inlet distributor and the filter medium within the filter tank. When a filtrate has to be sterilized, it is usual practice to arrange additionally a sterilizing device downstream of the filter.

A problem with downpipe filter device consist in that the filter may run dry during interruptions of operation or during intermittent operation which means that the liquid level falls below the level of the upper side of the filter. Further problem can arise when the sterilizing device becomes empty. Therefore it is necessary to provide the filter circuit which is provided upstream of the sterilizing device, with additional check- and flow control valves wherein, as it is known, one of the most difficult control problems has to be solved because of the intermittent filter/wash cycle of the filter device.

It is the object of the invention to provide a compact filter- and sterilizing apparatus having a simplified structure in which the function of the filter is assured anyway even with a variant supply or filter stand still.

For achieving this object, the filter- and sterilizing apparatus of the invention comprising a gravity filter device having a liquid supply, a downpipe filter and a clear liquid drainage as well as a sterilizing device hydraulically connected to the downpipe filter, characterized in that the sterilizing device connected to the clear liquid drainage of the downpipe filter, is adjustable in height and has the form of an supply channel to a over flow weir whereby the liquid level in the supply channel prior to the beginning of the filtration is adjustable to the same height as the water level in the downpipe filter above the filter medium.

The compact filter- and sterilizing apparatus described here, offers a surprising number of important technical advantages. No continuous control valves are necessary in the filter- and back-flashing circuit of the filter device in the filter- and sterilizing apparatus of the invention. Therefore an essential simplification for the construction of the filter- and sterilizing apparatus is achieved because the flow control device in the filter circuit which is difficult to produce and maybe produced only with high cost can be dispensed with.

Furthermore, an extremely reliable and error free sterilization of the clean water stream is achieved by means of the approach of the invention. Because of the simple and compact construction, the operational and maintenance time and effort is very low, and it has a minimum consumption of hydraulic energy because the continuous control valves are dispensed with. Furthermore, a small footprint of the complete filter- and sterilizing apparatus is achieved by the approach of the invention, since a lot of space is saved in between the components of the apparatus.

A further security measure for unusual disturbances of the operation consists in that the supply is switched off whereby the filter sterilizing apparatus goes into a waiting state in between to filtration cycles on its own. It is particularly surprising and important to note that also the danger of under-sterilization of the clean water in the sterilizing device with over flow weir according to the construction of the invention is avoided to a great extend even when the case of an intermittent filtrate supply happens.

According to an advantageous embodiment of the invention, the filter- and sterilizing apparatus is characterized in that the sterilizing device is an ultraviolet sluice. Ultraviolet cells are preferred in this application, and, with down pipe filter devices, they usually consist out of a closed tube which is provided with an intake and drainage stub each and which contains one or several ultraviolet lamps having a length of about 1.2 to 1.5 meters. For all of these ultraviolet cells to function probably, it is necessary that the cell body is always completely filled with water, and that no air is introduced due to supply variations or due to filter interruptions. This is a further reason why extensive control devices for the liquid level where necessary up to now. Consequently, by means of the inventive construction of the filter- and sterilizing apparatus, also the use of the ultraviolet cells was simplified and the operation thereof was improved.

According to an advantageous embodiment of the invention, the filter- and sterilizing apparatus is characterized in that a plurality of ultraviolet devices hydraulically connected in parallel, arranged next to each other and being adjustable in height are provided which is advantageous in particular with large liquid flow rates through the filter.

According to an advantageous embodiment of the invention, the filter- and sterilizing apparatus is characterized in that the plurality of ultraviolet devices hydraulically connected in parallel and arranged next to each other, are separately adjustable in height whereby the amount of liquid output from the sterilizing device is adjustable in an advantageously flexible way.

According to an advantageous embodiment of the invention, the filter- and sterilizing apparatus is characterized in that, in between the downpipe filter and the sterilizing device a check valve is provided. As check valves, simple valves like flap valves, ball valves or hose valves can advantageously be used. Furthermore, a simple and cost effective possibility for automatically switching on the check valve by means of pressurized air or power current is the result.

According to an advantageous embodiment of the invention, the filter- and sterilizing apparatus is characterized in that the check valve in between the downpipe filter and the sterilizing device is a slowly closing and opening check valve whereby the operational filter control becomes particularly smooth and free of shock.

According to an advantageous embodiment of the invention, the filter- and sterilizing apparatus is characterized in that the overflow weir comprises a V-shaped overflow which advantageously enables an accurate control of the overflow amount.

Embodiments of the invention are now explained with reference to the attached drawings in which:

FIG. 1 schematically shows the flow scheme of the gravity filter device of the invention having an ultra-violet sluice adjustable in height, and FIG. 2 shows an ultraviolet sluice.

As can be seen from FIG. 1, the raw water stream Q to be cleaned, flows through the conduit L1 and through the conduit L2 into the distributor trench V which is arranged at the top in the open filter tank F. The back flashing valve D is closed in this state.

The raw water stream Q flows across the rim of the distributor trench V and flows down to the liquid level N1. The water to be cleaned flows downwards through the filter medium M, is collected at the bottom of the downpipe filter F and flows from there through the conduit L3 to the distributor head V after having been cleaned of suspended materials. With the valves B and C closed and the valve A open, the filtrate flows through the conduit L4 into the ultraviolet sterilizing device, i.e. the ultraviolet sluice U, which is adjustable in height by means of a mechanical actuating device.

The ultraviolet sluice U is vertically adjustable in height by means of an actuating device and has the shape of a rectangular channel K which is delimited by the overflow weir Y.

The sterile water R flows across this overflow weir Y whereby a liquid level N2 is built up in the channel. The overflow weir Y may have the shape of a so called Thomson-weir with V-slit as is shown in FIG. 1. The cleaned, sterilized water R can also flow across the straight edge of the total channel breadth, i.e. as in a so called Bazin-weir. One or several ultraviolet lamps L are arranged submerged, i.e. below the liquid level N2, in the channel and sterilize the clear water stream.

The ultraviolet sluice U may be mechanically adjusted in height such that with shut down intake flow Q and open valve A, the liquid level N1 in the filter F is built up to several centimetres above the upper surface O of the filter medium M. It is ensured thereby that the filter medium M does not run dry during interruption of the filtering operation. Since the liquid level N1 and the liquid level N2 have approximately the same height upon still stand of the filter and opened valve A, it is ensured that the ultraviolet L or lamps are also arranged below the water when the filtering operation comes to a still stand.

During the filtering process, the liquid level N1 in the filter tank rises by 1 to 3 meters upon constant supply amount of the raw water Q. In contrast thereto, N2 remains nearly constant some centimetres above the edge of the weir drainage Y. In case the supply amount of raw water Q varies, for example by plus minus 15%, the water level N2 varies by a few millimetres.

As can be seen, the advantage of this gravity filter device with an ultraviolet sluice adjustable in height, is that a sterile and clean filtrate R leaves the apparatus even with varying intake of raw water Q and without using shut-off or control valves.

If, during continuous filtering, the liquid level N1 reaches roughly the overflow edge of the distributor trench V, the supply of raw water Q is interrupted, the valve A is closed, and the valve B is opened. Wash water W is pumped with high velocity from below through the conduit L5 and the conduit L3 into the filter bed. Because of this high velocity, the filter bed M is expended by about 15 to 25 vol.-%, and the contaminations adhering to the filter material, are washed away and flow upwards with the wash water stream into the distributor trench V and from there through L2 and the valve D into the wash water conduit L and form the wash water stream S. During the washing operation, the liquid level in the filter tank is above the overflow edge of the distributor trench V.

When the washing process of the filter medium is finished, the valves B and D are closed and the valve C is opened. The valve A remains closed at the moment until the so called "primary water" flowing through L7 and L6 is flowing out in a clear state and the water level N1 as lowered approximately to the liquid level N2. If this is the case, the valve C is closed and valve A is opened and a new filtering cycle with supply of raw water Q starts. An approximately equal water level or an equal liquid level is reached when the geometrical difference in height of N1 minus N2 amounts to less than about 10 centimetres.

As can be seen, the functional process of the total gravity filter device according to the invention is controlled with a few check valves. Because of the construction of the ultraviolet sluice U arranged in the cause of the filter circuit and being adjustable in height as channel with an overflow weir Y, furthermore, the amount of sterile water produced per hour can be accurately measured during the filtering process by a simple measurement of the level at the overflow weir.

The details of the ultraviolet sluice U adjustable in height, can be taken from FIG. 2. According to this, the ultraviolet sluice U which is adjustable in height, preferable has the shape of a rectangular channel K open at the top consisting out of a base plate UB, the two long side walls US and the back side UR relatively short as compared to the side walls. The back side UR contains through openings which are arranged below the water level N2. One or several sealed quartz tubes L extend into the channel through these openings. The ultraviolet radiators themselves having a length of about 1.2 to about 1.6 meters, are in the quartz tubes.

In practise, one will use at least two ultraviolet radiators in order to ensure that the function to sterilize the clean water stream, is not lost upon breakdown of a radiator. One of the long side surfaces US contains a tube stub to which the intake tube conduit L4 is connected, at the corner to the UR, as can be seen from FIG. 2.

As can be seen, the ultraviolet sluice U adjustable in height is closed at its front end by means of the overflow weir Y across which the sterile water stream R is drained. Preferably, the ultraviolet sluice U adjustable in height is closed by a cover UD at its top. The cover UD is best designed such that it can be removed easily. Thereby, an inspection of the ultraviolet sluice is facilitated, and one can easily clean it in case of the necessity of cleaning without having to demount the ultraviolet sluice adjustable in height.

In another embodiment, the filter- and sterilizing apparatus according to the invention contains several ultraviolet devices arranged in parallel next to each other and being adjustable in height of the above kind. These ultraviolet devices arranged in parallel to each other, are for example supplied with filtrate water from a common conduit L4, and this kind of connecting the filter- and sterilizing apparatus to each other is advantageous in cases where large water streams are to be sterilized.

The invention claimed is:

1. Filter and sterilizing apparatus comprising:
   a. a raw water inlet;
   b. a downpipe filter formed as a gravity filter and connected to said raw water inlet;
   c. a clean liquid drainage line for cleaned water leading away from said downpipe filter; and,
   d. a sterilizing device hydraulically connected to said clean liquid drainage line of said downpipe filter, said sterilizing device being adjustable in height and configured as a supply channel leading to an overflow weir, a liquid level associated with said supply channel being adjustable to correspond to a liquid level associated with a water level above filter medium of said downpipe filter by adjusting a mounting height of said sterilizing device.

2. Apparatus according to claim 1 wherein said sterilizing device is an ultraviolet sluice.

3. Apparatus according to claim 1 wherein said sterilizing device comprises several ultraviolet devices hydraulically connected in parallel, said several ultraviolet devices arranged next to each other and being adjustable in height.

4. Apparatus according to claim 3 wherein said several ultraviolet devices hydraulically connected in parallel, said several ultraviolet devices arranged next to each other, each being separately adjustable in height.

5. Apparatus according to claim 1 wherein a check valve is provided in between said downpipe filter and said sterilizing device.

6. Apparatus according to claim 1 wherein a slow closing/opening check valve is provided in between said downpipe filter and said sterilizing device.

7. Apparatus according to claim 1 wherein said overflow weir is a V-shaped overflow.

* * * * *